United States Patent
Keränen

(10) Patent No.: US 11,273,039 B2
(45) Date of Patent: Mar. 15, 2022

(54) DEVICE AND A METHOD FOR IMPROVING THE FUNCTION OF A HEART VALVE

(71) Applicant: Medtentia International Ltd Oy, Helsinki (FI)

(72) Inventor: Olli Keränen, Bjärred (SE)

(73) Assignee: Medtentia International Ltd Oy, Espoo (FI)

( * ) Notice: Subject to any disclaimer, the term of this patent is extended or adjusted under 35 U.S.C. 154(b) by 0 days.

(21) Appl. No.: 16/231,337

(22) Filed: Dec. 21, 2018

(65) Prior Publication Data

US 2019/0240021 A1 Aug. 8, 2019

Related U.S. Application Data

(63) Continuation of application No. 14/357,760, filed as application No. PCT/EP2012/072272 on Nov. 9, 2012, now Pat. No. 10,172,711.

(Continued)

(30) Foreign Application Priority Data

Nov. 10, 2011 (EP) ..................................... 11188656

(51) Int. Cl.
*A61F 2/24* (2006.01)

(52) U.S. Cl.
CPC .......... *A61F 2/2463* (2013.01); *A61F 2/2445* (2013.01); *A61F 2/2454* (2013.01);
(Continued)

(58) Field of Classification Search
CPC .............................. A61F 2/2463; A61F 2/2445
See application file for complete search history.

(56) References Cited

U.S. PATENT DOCUMENTS

| | | |
|---|---|---|
| 2002/0095167 A1 | 7/2002 | Liddicoat et al. |
| 2004/0106989 A1 | 6/2004 | Wilson et al. |

(Continued)

FOREIGN PATENT DOCUMENTS

| | | |
|---|---|---|
| JP | 2007536989 A | 12/2007 |
| WO | WO2007/138571 A2 | 12/2007 |
| WO | WO2011047168 A1 | 4/2011 |

OTHER PUBLICATIONS

WIPO, European International Preliminary Examining Authority, International Preliminary Report on Patentability dated Jan. 14, 2014 in International Patent Application No. PCT/EP2012/072272, 15 pages.

(Continued)

*Primary Examiner* — Leslie Lopez
(74) *Attorney, Agent, or Firm* — Inskeep IP Group, Inc.

(57) ABSTRACT

A medical device is disclosed that reinforces weakened or degenerated areas of at least a portion of a leaflet (24) Of the heart valve. Function of a heart valve is thus improved. The medical device comprises at least a first partly flexible leaflet reinforcement patch (30) having an extension between an inner section (34) and an outer section (32), wherein said outer section (32) is configured to be oriented towards said annulus,and said inner section (34) is configured to be oriented towards said inner section of said valve tissue, and at least a portion of said inner section (34) of said flexible leaflet reinforcement patch (32) having at least one of said plurality of leaflets (24) in juxtaposition to said portion of said inner section (34), and said portion of said inner section (34) being positioned to provide reinforcement to said plurality of leaflets (24).

10 Claims, 8 Drawing Sheets

Related U.S. Application Data

(60) Provisional application No. 61/558,787, filed on Nov. 11, 2011.

(52) U.S. Cl.
CPC ............ *A61F 2220/0016* (2013.01); *A61F 2230/0091* (2013.01)

(56) References Cited

U.S. PATENT DOCUMENTS

| | | | |
|---|---|---|---|
| 2004/0143323 A1* | 7/2004 | Chawla | A61F 2/2457 623/2.12 |
| 2005/0107871 A1 | 5/2005 | Realyvasquez et al. | |
| 2005/0149178 A1 | 7/2005 | Spence | |
| 2009/0198324 A1* | 8/2009 | Orlov | A61B 17/115 623/2.37 |
| 2009/0264995 A1* | 10/2009 | Subramanian | A61F 2/2454 623/2.36 |
| 2010/0121437 A1 | 5/2010 | Subramanian et al. | |
| 2010/0145440 A1* | 6/2010 | Keranen | A61F 2/2448 623/2.37 |
| 2011/0190879 A1 | 8/2011 | Bobo et al. | |

OTHER PUBLICATIONS

WIPO, European International Search Authority, International Search Report dated Dec. 21, 2012 in International Patent Application No. PCT/EP2012/072272, 4 pages.

\* cited by examiner

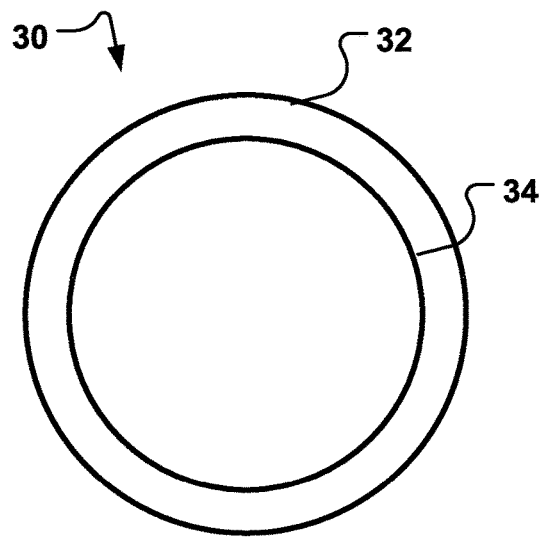 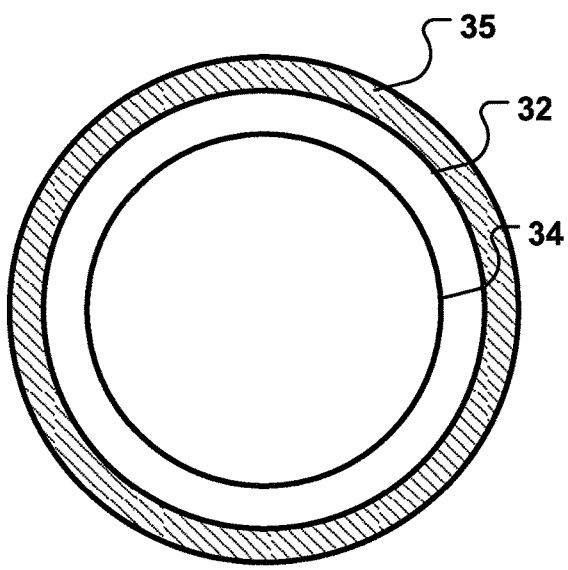
Fig. 3AFig. 3B
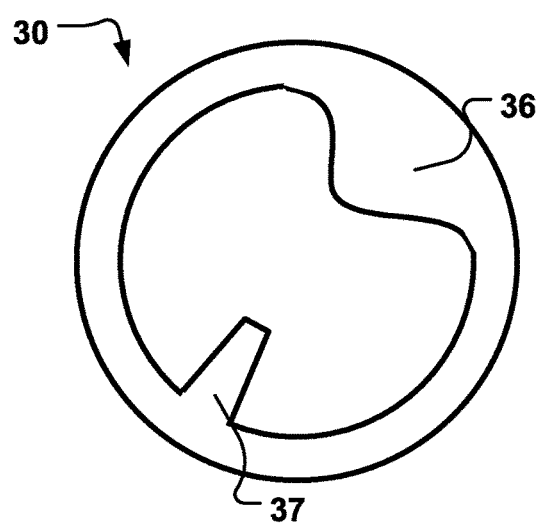 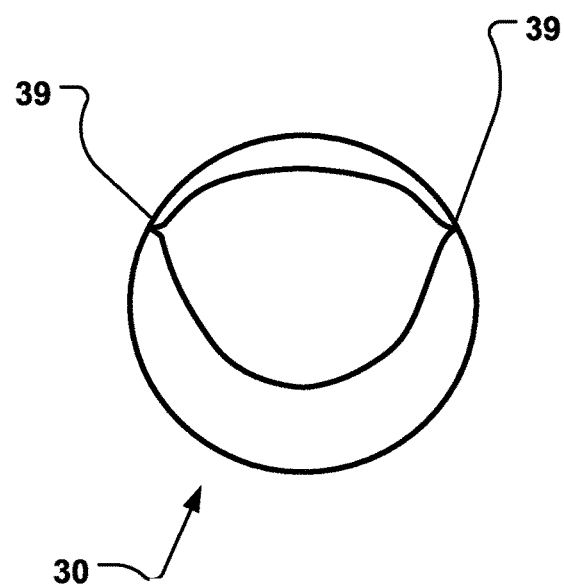
Fig. 3CFig. 3D

DEVICE AND A METHOD FOR IMPROVING THE FUNCTION OF A HEART VALVE

RELATED APPLICATIONS

This application is a continuation of U.S. patent application Ser. No. 14/357,760 filed May 12, 2014 entitled A Device And A Method For Improving The Function Of A Heart Valve, which is the U.S. National Phase of and claims priority to International Patent Application No. PCT/EP2012/072272, International Filing Date Nov. 9, 2012, entitled A Device And A Method For Improving The Function Of A Heart Valve, which claims benefit of European Patent Application No. EP11188656.0 filed Nov. 10, 2011 entitled A Device And a Method For Improving The Function Of A Heart Valve, and of U.S. Provisional Application Ser. No. 61/558,787, filed Nov. 11, 2011 entitled A Device And a Method For Improving The Function Of A Heart Valve, all of which are incorporated herein by reference in their entireties.

FIELD OF THE INVENTION

This disclosure pertains in general to the field of medical devices and methods. More particularly, the disclosure relates to a medical device for improving the function of a heart valve, and in particular to improving leaflets thereof.

BACKGROUND OF THE INVENTION

FIG. 1 illustrates a portion of the heart 12, the mitral valve 18, and the left ventricle 14. The mitral valve is at its boundary circumferenced by an annulus 20. The valve has two cusps or leaflets 22, 24. Each of these cusps or leaflets 22, 24 are connected to a respective papillary muscle 27, 29 via their respective connecting chordae 26, 28. In normal healthy individuals the free edges of the opposing leaflets will close the valve. However, for some individuals the closure is not complete, which results in a regurgitation, also called valvular insufficiency, i.e. back flow of blood to the left atrium making the heart less effective and with potentially severe consequences for the patient. FIG. 2 illustrates a mitral valve 18, in which the leaflets 22, 24 do not close properly. This commonly occurs when the annulus 20 becomes dilated. One surgical procedure to correct this is to remove a portion of the leaflet 24 and stitch the cut edges together with one another. The procedure will pull back the annulus 20 to a more normal position. However the strength of the leaflet 24 is altered. Similar problems with a less effective heart function occur if one or both leaflets are perforated to such an extent that blood is flowing towards the left atrium, although the leaflets close properly.

In some conditions of degenerated heart function, the leaflets do not present a solid surface, as in a degenerative valve disease. The leaflet could also be perforated, with one or several holes, where the blood can flow backwards into the atrium.

Another possibility is that the leaflet is ruptured, most commonly at an edge of a leaflet, resulting in an incomplete coaptation. In some conditions of degenerated heart function, the leaflets do not present a solid surface, e.g. degenerative valve disease. The leaflet could be perforated, with one or several holes, where the blood can flow backwards into the atrium. Another possibility is that the leaflet is ruptured, most commonly at an edge of a leaflet, resulting in an incomplete coaptation.

US2005/0107871 discloses a valve implant or prosthesis which includes a skirt or prosthetic valve leaflet configured to cover one of the leaflets of the valve to be repaired in a patient's heart. In one embodiment, a heart valve prosthesis includes a curved member and a skirt. The curved member can have first and second ends and be adapted to form a partial ring along a portion of one of the valve annulae in the patient's heart. Alternatively, the curved member can form a full ring that is adapted to extend along the entire valve annulus. The skirt extends along the curved member and depends therefrom. This prosthesis Is especially useful in treating mitral valve insufficiency. In this case, the skirt can be configured so that when the prosthesis Is secured to the mitral valve along the mitral valve annulus, the skirt covers the posterior leaflet and the opposed edges of the skirt and the anterior leaflet coapt. In addition, when the curved member is secured to the posterior portion of the mitral valve annulus, further annulus dilation can be minimized or eliminated.

Hence, a medical device and method would be advantageous, and in particular such a device and method allowing for repair of one or more leaflets of a heart valve, or other related anatomical structures, such as the chordae attached to the ventricular side of leaflets.

From US2004/IO6989 a support for providing additional strength to existing regurgitant or prolapsed valve leaflets is known. The support restores an otherwise non-functioning, or poorly functioning, native valve to a functioning condition, obviating the need for a complete valve removal or replacement. The support may also be applied to a functioning valve leaflet as a prophylactic measure against future failure. The delivery method includes a delivery mechanism for attaching the support to the native valve leaflet.

However, the support disclosed in this document may not be rigid enough. Furthermore, the support may not be easy to handle by the surgeon during surgery.

SUMMARY OF THE INVENTION

Accordingly, embodiments of the present disclosure preferably seeks to mitigate, alleviate or eliminate one or more deficiencies, disadvantages or issues in the art, such as the above-identified, singly or in any combination by providing a device and a method, that improves the function of a heart valve comprised of valve tissue including an annulus at an outer section of the valve tissue and a plurality of leaflets at an inner section of the valve tissue, according to the appended patent claims.

According to a first aspect of the disclosure, a medical device is provided for improving the function of a heart valve. The medical device has a flexible leaflet reinforcement patch, which has at least partly an extension between an inner portion and an outer portion thereof. The outer portion of the flexible leaflet reinforcement patch is during use oriented towards the annulus of a cardiac valve, away from one or more of a plurality of leaflets thereof. The inner portion is oriented towards the inner section of leaflet tissue of the cardiac valve. The inner portion of the leaflet is oriented towards the centre of the valve. At least a part of the inner portion of the flexible leaflet reinforcement patch is in juxtaposition to at least one leaflet. The inner part of the flexible leaflet reinforcement patch, which is in juxtaposition to at least one of the leaflets is positioned in such a manner that it provides reinforcement to at least a portion of one of the plurality of leaflets.

According to a second aspect of the disclosure, a method for improving the function of a heart valve is provided. By placing the flexible leaflet reinforcement patch in such a manner as to orient its outer section towards the annulus and to orient the inner section towards an inner section of the valve tissue a circumferential proportion of the heart valve and leaflets are engaged with the flexible leaflet reinforcement patch. The flexible leaflet reinforcement patch is placed so that it has at least a portion of one of the plurality of leaflets in juxtaposition, so as to provide reinforcement to the leaflet portion or portions.

According to a third aspect of the disclosure, a medical device for improving the function of a heart valve, comprising valve tissue including an annulus and a plurality of leaflets is provided. The medical device comprises a tissue anchoring unit, such as a first loop-shaped support, configured to abut a first side of the heart valve. The medical device further comprises a first flexible leaflet reinforcement patch, being connected by a connection portion to the abutted tissue anchoring unit, and at least a portion of the leaflet reinforcement patch is in juxtaposition with at least one leaflet. The flexible leaflet reinforcement patch is configured to provide reinforcement to the at least one leaflet.

Further embodiments are defined in the dependent claims, wherein features for the second and subsequent aspects of the disclosure are as for the first aspect mutatis mutandis.

Some embodiments have a tissue anchoring unit that is connected to the outer surface of the flexible leaflet reinforcement patch. The tissue anchoring unit, when in use, secures the flexible leaflet reinforcement patch to the adjacent tissue and/or annulus, in such a manner that the flexible leaflet reinforcement patch is prevented from dislocating itself, without loss of the desired reinforcement function. Hence, the flexible leaflet reinforcement patch will be less affected by the forces of the pulsatile blood flow and the dynamics of the beating heart, which would dislocate the flexible leaflet reinforcement patch otherwise.

The tissue anchoring unit for some embodiments is a loop-shaped support. This gives a more rigid construction that abuts against the whole extension of adjacent valve tissue, e.g. the annulus. The medical device is easier to handle by the surgeon during surgery.

Some embodiments have a tissue anchoring unit which has fastening units as glue, spikes, prongs, points, hooks, clasps or hasps. These fastenings units further secure attachment of the medical device to adjacent valve tissue, e.g. annulus. The fastening units are in some embodiments made of a biocompatible material. In other embodiments these fastening units are made of biodegradable material or bioabsorbable material. The latter embodiments act to reinforce the leaflets during a restricted period of time, as and when required.

Some embodiments have portions of the flexible leaflet reinforcement patch at least partly extending from the outer section of the valve tissue to a free edge of a leaflet. These embodiments will reinforce the whole radial extension of the leaflet, e.g. by patching over the sewing line where a leaflet section has been removed and the opposing cut edges have been surgically attached together.

Some embodiments have the thickness of the flexible leaflet reinforcement patch thinner than the extension of flexible leaflet reinforcement patch. The thickness of the flexible leaflet reinforcement patch is for some embodiments at least partly uniform. This does not restrain and affect the natural movement of the leaflet during heart movements. Having the flexible leaflet reinforcement patch at least uniform in thickness allows for individual patient configuration to facilitate that the flexible leaflet reinforcement patch's thickness reinforces weakened or degenerated areas of at least a portion of a leaflet.

Some embodiments have the inner portion of the flexible leaflet reinforcement patch that will grow into a leaflet where the flexible leaflet reinforcement patch is in juxtaposition against the leaflet. This gives a permanent reinforcement of the leaflet area. Furthermore, some embodiments have its inner portion made of a biocompatible material. As such the medical device will not interfere with the valve tissue, avoiding rejection reactions, and/or avoids causing of blood clotting, embolies, blood cavitations, or turbulences in the blood flow passing the heart valve.

Some embodiments have the inner portion of the flexible leaflet reinforcement patch made of a biodegradable material and/or a bio absorbable material. These embodiments will give a temporary reinforcement of the leaflet area until the leaflet is restored to a healthy condition. The time span of the temporary reinforcement is controlled upon specification of the biodegradable material and/or a bio absorbable material.

Some embodiments have fastening units at the inner portion of the flexible leaflet reinforcement patch in juxtaposition to the leaflet. These fastening units are e.g. glue, spikes, prongs, points, hooks, clasps or hasps. In use these fastening units prevent the leaflet reinforcement patch from vertically dislocating until the leaflet has firmly grown into the leaflet or the leaflet reinforcement patch is absorbed or degraded.

Some embodiments have an inner portion of the flexible leaflet reinforcement patch for attaching a first end of a string. The other end of the string is to be connected to a cardiac structure other than a leaflet. These embodiments preserve the natural leaflet if securing in the free edge of the leaflet is prevented due to e.g. degeneration of the leaflet. In some embodiments the cardiac structure is a papillary muscle and the string is a chordae replacement unit. In use, these embodiments maintain the natural dynamics of the heart, while replacing one or several chordae with one or several replacement units. These strings are made of biocompatible material, such as artificial or biological material.

Some embodiments have at least one string extending from the inner portion of the flexible leaflet reinforcement patch. The free end of the string is in use connected to a cardiac structure other than a leaflet. These embodiments preserve the natural leaflet if securing in the free edge of the leaflet is prevented due to e.g. degeneration of the leaflet. In some embodiments the free end of the string is connected to the papillary muscle. Moreover, in use these embodiments maintain the natural dynamics of the heart while adding one or several artificial chordae as replacement units.

Some embodiments provide a method for anchoring the flexible leaflet reinforcement patch in the heart valve tissue including a tissue anchoring unit. The flexible leaflet reinforcement patch will thus be securely attached to the adjacent heart tissue and also make the flexible leaflet reinforcement patch less affected by the dynamic forces of pulsatile blood flow and dynamic movements of the beating heart.

Some embodiments provide for a method for placing the flexible leaflet reinforcement patch's inner section in juxtaposition against at least a portion of at least one of the leaflets. The placement includes connecting at least one string to a cardiac structure other than a leaflet.

Some embodiments have a first loop-shaped support which in use abuts a first side of the heart valve. Connected to the first loop-shaped support is a first flexible leaflet reinforcement patch at a connecting surface. When first loop-shaped support is abutting the heart valve, the first flexible leaflet reinforcement patch is arranged so that in use, the patch is in juxtaposition to at least a portion of one of the leaflets. The connected flexible leaflet reinforcement patch is configured to provide reinforcement to at least one of the leaflets.

Some embodiments have a tissue anchoring unit, which in use anchor the medical device to a first side of the heart valve. To the anchoring unit a flexible leaflet reinforcement patch is attached, and the flexible leaflet reinforcement patch has a leaflet in juxtaposition to the inner section. When in use, the section in juxtaposition is arranged against at least a portion of at least one leaflet, when the anchoring unit is fixed in the heart valve. The flexible leaflet reinforcement patch reinforces at least one of the leaflets when in juxtaposition to the leaflet.

Some embodiments have a first loop-shaped support as the tissue anchoring unit. The first loop-shaped support gives enhanced rigidity to the medical device and furthermore makes the device more manageable at implantation. Moreover, the medical device will be juxtaposed with valve tissue throughout the circumferential extension of the anchoring unit.

In some embodiments, the flexible leaflet reinforcement patch has a plurality of separate flexible leaflet reinforcement patch units. In use these individual extending flexible leaflet reinforcement patch units independently extend towards the centre of the valve. An induced dislocation of a single leaflet reinforcement patch unit is effectively isolated and thus will not pull and dislocate adjacent leaflet reinforcement patch units.

For some embodiments, the thickness of the leaflet reinforcement patch is at least partly uniform. The leaflet reinforcement patch does not affect the natural movement of the leaflet by adding extra weight or rigidity at portion of the leaflet, where it is not needed.

In some embodiments the leaflet reinforcement patch extends at least partly to the free edge of at least one of the plurality of leaflets.

In some embodiments, the whole extension of the leaflet will be covered and reinforced by the leaflet reinforcement patch.

Some embodiments provide for a catheter-based delivery without leakage or regurgitation.

Some embodiments provide for sealing of the area between a stent and a replacement heart valve.

Some embodiments provide good adherence between two metal parts and sealing of the area between the two metal parts, at a target site, such as a mitral valve.

Embodiments provide for advantageous medical devices and/or methods for facilitating and/or providing treatment of regurgitation of mitral and tricuspid valves.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of the embodiments that the disclosure is capable of will be apparent and elucidated from the following description of embodiments of the present disclosure, reference being made to the accompanying drawings, in which

FIG. 3A illustrates the flexible leaflet reinforcement patch;

FIG. 3B illustrates the flexible leaflet reinforcement patch with an anchor unit attached;

FIG. 3C illustrates example of extensions of the inner section of the flexible leaflet reinforcement patch;

FIG. 3D illustrates a flexible leaflet reinforcement patch with adaptations matching the commissures;

DESCRIPTION OF EMBODIMENTS

Figure 1:
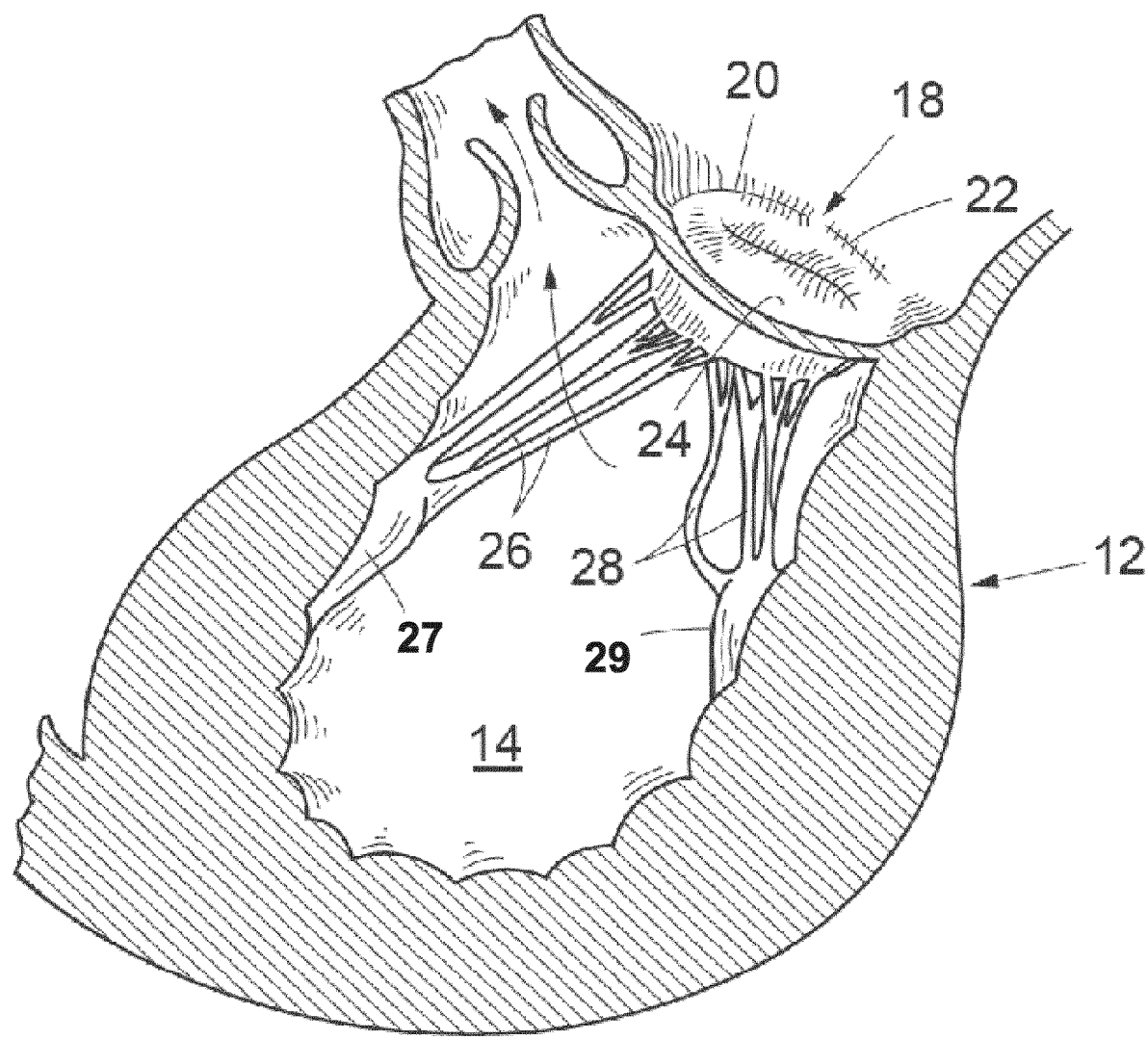
FIG. 1 is a cross-sectional view of the left ventricle of the heart. The figure illustrates the mitral valve, corresponding papillary muscles and the connecting chordae.

Specific embodiments of the disclosure now will be described with reference to the accompanying drawings. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. The terminology used in the detailed description of the embodiments illustrated in the accompanying drawings is not intended to be limiting of the disclosure. In the drawings, like numbers refer to like elements.

The description is illustrated with reasoning using the mitral valve as a starting point. However it should be understood that the methods and devices of this disclosure could be applied also to e.g. the tricuspid valve, the aortic valve or the pulmonary valve.

FIG. 1 illustrates a portion of the heart 12, the mitral valve 18, and the left ventricle 14. The mitral valve is at its boundary encompassed by an annulus 20. The valve has two cusps or leaflets 22, 24. Each of these cusps or leaflets 22, 24 are connected to its respective papillary muscle, 27, 29 via respectively connecting chordae 26, 28. In healthy individuals, the free edges of the opposing leaflets will close the valve. However, for some individuals, the closure is not complete which results in a regurgitation, also called valvular insufficiency, i.e. a back flow of blood to the left atrium making the heart less effective and potentially with severe consequences for the patient.

Figure 2:
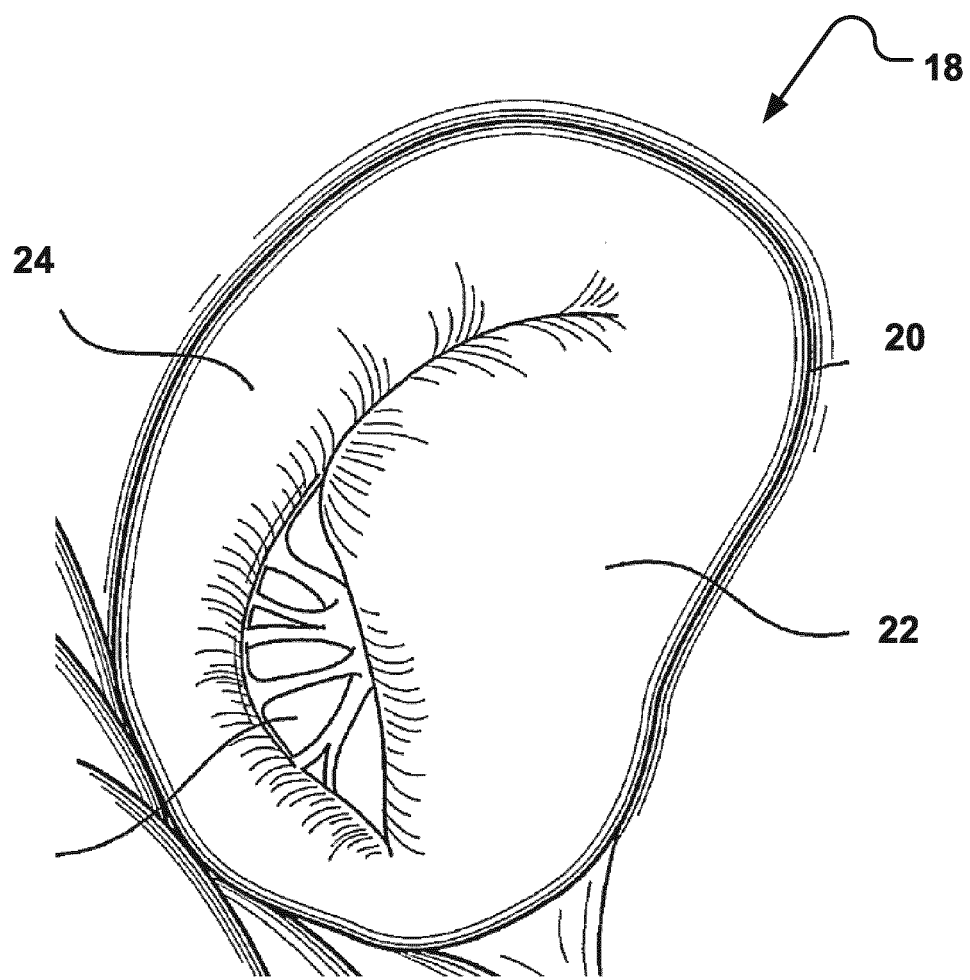
FIG. 2 is a plan view of the mitral valve.

FIG. 2 illustrates the mitral valve 18 having the leaflets not closing properly. This commonly occurs when the annulus becomes dilated. One surgical procedure to correct this is to remove a portion of the leaflet and stitch the cut edges together with one another. The procedure will pull back the annulus to a more normal position. However the strength of the leaflet is altered. Similar problems, with a less effective heart function, occur if one or both leaflets are perforated to such an extent that blood is flowing towards the left atrium, although the leaflets close properly.

In an embodiment of the disclosure according to FIG. 3A, a flexible leaflet reinforcement patch 30 is illustrated with an extension between an inner section 34 and an outer section 32. The outer section of the flexible leaflet reinforcement patch 30 is configured to be oriented towards the annulus, and the inner portion of the flexible leaflet reinforcement patch 30 is configured to be oriented towards the inner section of the valve tissue, i.e. towards the centre of the valve. The flexible leaflet reinforcement patch has at least a portion of the inner section 34 of the flexible leaflet reinforcement patch in juxtaposition to a portion of a leaflet. When in use, the portion of the flexible leaflet reinforcement patch 30, which is in juxtaposition to at least one portion of the plurality of leaflets, is arranged in a manner so as to provide reinforcement to the leaflet portions. Thus, the flexible leaflet reinforcement patch 30 provides reinforcement for a leaflet portion which either has become degenerated or damaged or provides reinforcement for a leaflet portion where a portion has been surgically removed, i.e. the flexible leaflet reinforcement patch 30 is used for repair and/or replacement of a leaflet or a portion thereof.

Some embodiments have a tissue anchoring unit 35, shown in FIG. 3B, configured to anchor the medical device to a first side of the heart valve. These embodiments have a leaflet reinforcement patch, which is connected to the tissue anchoring unit 35. The leaflet reinforcement patch 30 has a leaflet in juxtaposition to a portion of the leaflet reinforcement patch 30, which is configured to be arranged in juxtaposition against at least a portion of at least one of the leaflets, when the anchoring unit is fixed to the heart valve. The connected leaflet reinforcement patch 30 is configured to provide reinforcement to at least one of the leaflets, when at least a portion is in juxtaposition against the leaflet. In the embodiment of the disclosure illustrated in FIG. 3b, a tissue anchoring unit 35 is connected at the outer section 32 of the flexible leaflet reinforcement patch 30. The tissue anchoring unit 35 provides for an opportunity to secure or anchor the flexible leaflet reinforcement patch 30 to adjacent heart tissue and/or annulus. Thus the flexible leaflet reinforcement patch 30 is prevented from dislocating itself, with loss of the desired reinforcement function. Moreover, the flexible leaflet reinforcement patch 30 will be less affected by the force of the pulsatile blood flow and the dynamics of the beating heart.

The tissue anchoring unit 35 for some of the embodiments is a first loop-shaped support. The loop-shaped support presents a more rigid construction and also provides an abutment against the whole extension of the annulus, which further contributes to the rigidity of the construction. The rigidity of the loop-shaped support can be soft or very firm depending on the material, e.g. plastic, shape memory polymer, cloth or fabric, multilayered stitched and reinforced, and metal, such as titanium, stainless steel or nitinol. The gained rigidity may potentially yield the medical device to be easier to handle in the surgical situation with regards to implantation of the medical device.

The tissue anchoring unit 35 has fastening units in some embodiments. The fastening units are glue, spikes, prongs, points, hooks, clasps or hasps. The fastenings units will further firmly secure attachment of the medical device to adjacent valve tissue and are in some embodiments made of a biocompatible material. In other embodiments these fastening units are made of biodegradable material or bioabsorbable material. By having fastening units of biodegradable material or bioabsorbable material, a time dependent attachment of the flexible leaflet reinforcement patch 30 due to the speed of degradation and/or absorption is possible. Until the inner portion is securely incorporated into the leaflets, the fastening units hold the outer sections of the leaflet reinforcement patch, adjacent to the annulus. The desired position of the inner portion is preserved and will be incorporated into the surrounding tissue.

In one embodiment depicted in FIG. 3C, the extension of the flexible leaflet reinforcement patch 30 is at least partly configured for extending from the outer section of the valve tissue to a free edge of the at least one of the plurality of leaflets, with an extension, such as a wave-shaped extension 36. Alternatively the flexible leaflet reinforcement patch 30 has a rectangular-shaped extension 37. However, it should be understood that any other suitable shape of the extension may be used. The extension of the flexible leaflet reinforcement patch 30 can be along the whole extension of the leaflet towards the free-edge of the leaflet. This minimizes unwanted force concentrations at the transition edge between the flexible leaflet reinforcement patch 30 and the leaflet. Adjacent to the edge of the flexible leaflet reinforcement patch 30 is where the leaflet is exposed to the highest force. By extending the flexible leaflet reinforcement patch 30, this force concentration is eliminated and potential rupture of the leaflet is avoided. Patching over the sewing line is advantageous, especially in those instances where a leaflet section has been removed and the opposing cut edges has been surgically attached together strengthening the leaflet area.

Shown in FIG. 3D is a flexible leaflet reinforcement patch 30 having a more anatomic configuration, shaped for a better fit with parts of the heart. The indentation 39 corresponds to a commissure of the heart valve, and the flexible leaflet reinforcement patch 30 does not extend beyond the commissure. The blood flow pattern from the left atrium to the left ventricle is kept as natural as possible and as such does not cause turbulent or constricted blood flow. When a flexible leaflet reinforcement patch 30 extends over the commissure, a free edge of the flexible leaflet reinforcement patch 30 is exposed so that the dynamics of the beating heart, i.e. movements and pulsatile blood flow, can pull and tear the flexible leaflet reinforcement patch 30.

Figure 4:
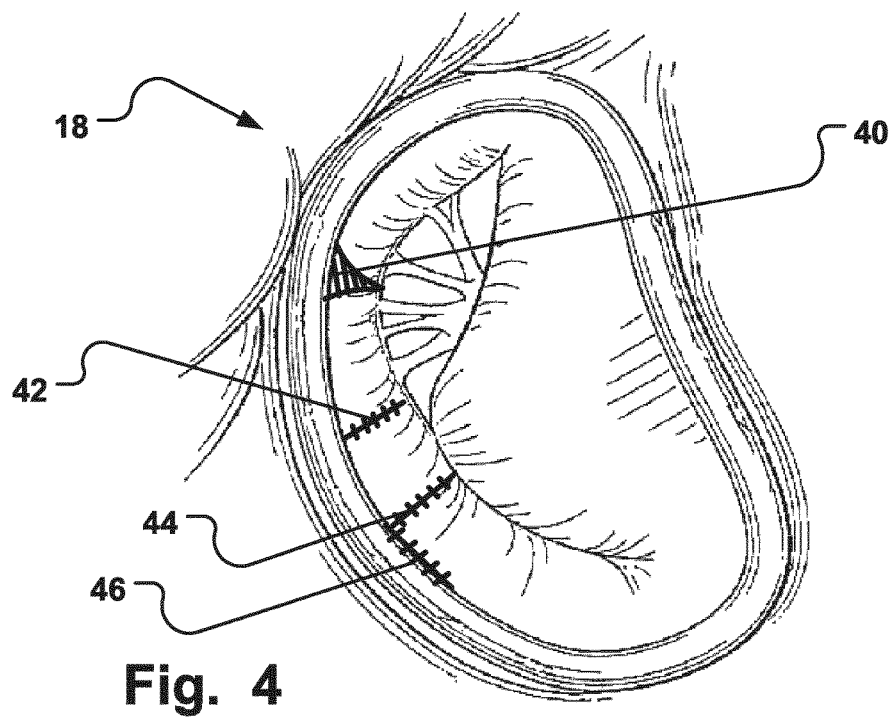
FIG. 4 is a plan view of the mitral valve, illustrating surgical intervention and resulting stitches.

The surgical procedure is illustrated in FIG. 4, where a leaflet-ectomy may be surgically removing a piece of the leaflet resembling a sector of a circle 40 and stitching the radial edges of the leaflet together with one another 42. A different procedure, so called sliding, involves making cuts in the leaflet along and adjacent to the annulus and one cut in the leaflet towards the centre of the valve. Next a radial piece of the leaflet is removed, in such a manner as to reduce the circumference of the outer section of the leaflet. The procedure yields commonly L- or T-shaped formations of stitches and sewing lines, one line of stitches along the annulus 46 and one line of stitches inwardly towards the centre of the valve 44.

Figure 5:
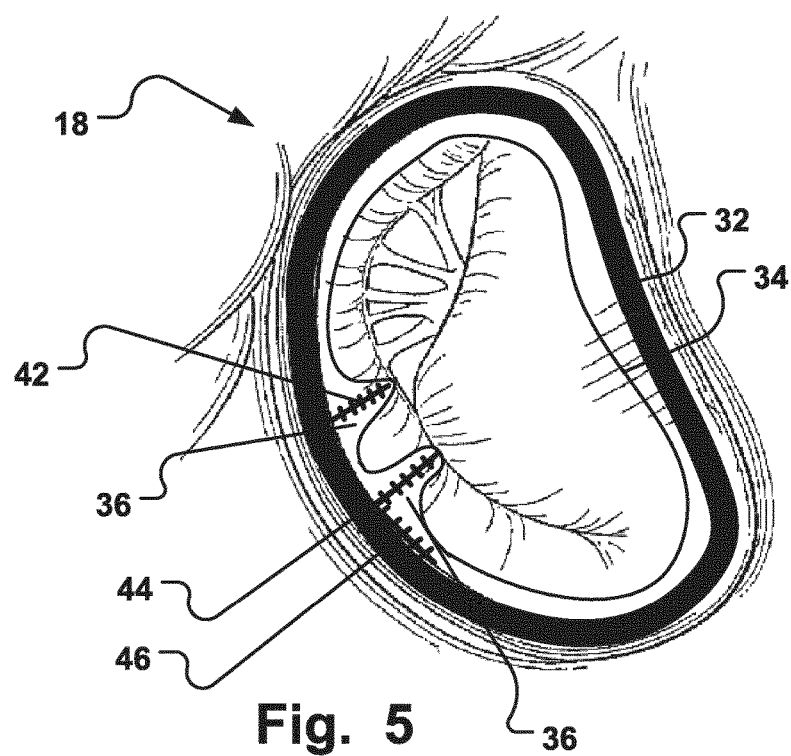
FIG. 5; is a plan view of the mitral valve, illustrating a flexible leaflet reinforcement patch in juxtaposition to surgical intervention areas of the leaflet.

In an embodiment according to FIG. 5, the flexible leaflet reinforcement patch 30 is in position at the heart valve with the outer section 32 towards the annulus and the inner section 34 towards the centre of the heart valve. As shown in FIG. 5, the inner section 34 of the flexible leaflet reinforcement patch 30 extends, with an extension, such as the wave-shaped extension 36, radially inwards over the stitched areas of the leaflet to reinforce the leaflet. Thus, the flexible leaflet reinforcement patch 30 reinforces the leaflet.

In addition, the outer section 32 of the flexible leaflet reinforcement patch 30 is during use oriented towards the annulus of the cardiac valve, in this case a mitral valve, and since the flexible leaflet reinforcement patch 30 is in close contact with the annulus, the area between the annulus and the outer section 32 of the flexible leaflet reinforcement patch 30 is sealed.

The material of the flexible leaflet reinforcement patch 30 is flexible in at least two aspects; firstly not to negatively affect the natural movement of the leaflet during the cycle of a heart beat, secondly to allow, at implantation of the medical device, adjustment of the medical device to properly match the anatomic structure of the implantation site. This latter flexibility of the leaflet reinforcement patch is due to expected anatomic variations between different patients.

In some embodiments, the flexible leaflet reinforcement patch 30 also has a thickness, which is thinner than the extension of the flexible leaflet reinforcement patch 30. The thickness of the flexible leaflet reinforcement patch 30 is at least partly non-uniform, such that the flexible leaflet reinforcement patch 30 is e.g. thicker at certain areas in juxtaposition to the flexible leaflet reinforcement patch 30, i.e. where a larger force is anticipated or another higher demand is likely. Thus, the leaflet reinforcement patch can be devised with a variation in thickness so as to be precisely tailored to the specific need required. With similar reasoning, a thinner proportion of a segment of the flexible leaflet reinforcement patch 30 may be advantageous, e.g. to not prevent the natural movement of the leaflet where no reinforcement is required. The thickness of the flexible leaflet reinforcement patch 30 is configured at least partly to be appositioned with weakened or degenerated areas of at least a portion the leaflets.

Some embodiments have an inner section 34 of the flexible leaflet reinforcement patch 30, which is incorporated into at least one of the plurality of leaflets. These embodiments give a permanent reinforcement of the leaflet area where the flexible leaflet reinforcement patch 30 has been integrated. Furthermore, some embodiments have the inner section 34 made of a biocompatible material. As such the medical device will not inflict with and/or cause blood clotting. In addition, in some embodiments the inner section 34 of the flexible leaflet reinforcement patch 30 is made of a biodegradable material and/or a bioabsorbable material. These choices of material provide a temporary reinforcement of the leaflet area until the leaflet is restored to a healthy condition, which may be beneficial in some circumstances, e.g. for young patients, whose hearts are still growing, since in young patients, with growing hearts, a non-degradable or non-absorbable leaflet reinforcement patch may disturb the growth of the heart valve. The time span of the temporary reinforcement may be controlled upon choice of specification of the biodegradable material and/or the bio absorbable material.

Some embodiments provide for a leaflet in juxtaposition to a portion of the flexible leaflet reinforcement patch's inner section 34 by comprising fastening means, e.g. glue, spikes, prongs, points, hooks, clasps or hasps. By having such fastening means for portions of the flexible leaflet reinforcement patches 30 in juxtaposition to the leaflet, the leaflet reinforcement patch is prevented from vertically dislocating until the leaflet reinforcement patch is firmly integrated into the leaflet or the flexible leaflet reinforcement patch 30 is absorbed or degraded properly.

Figures 6, 7:
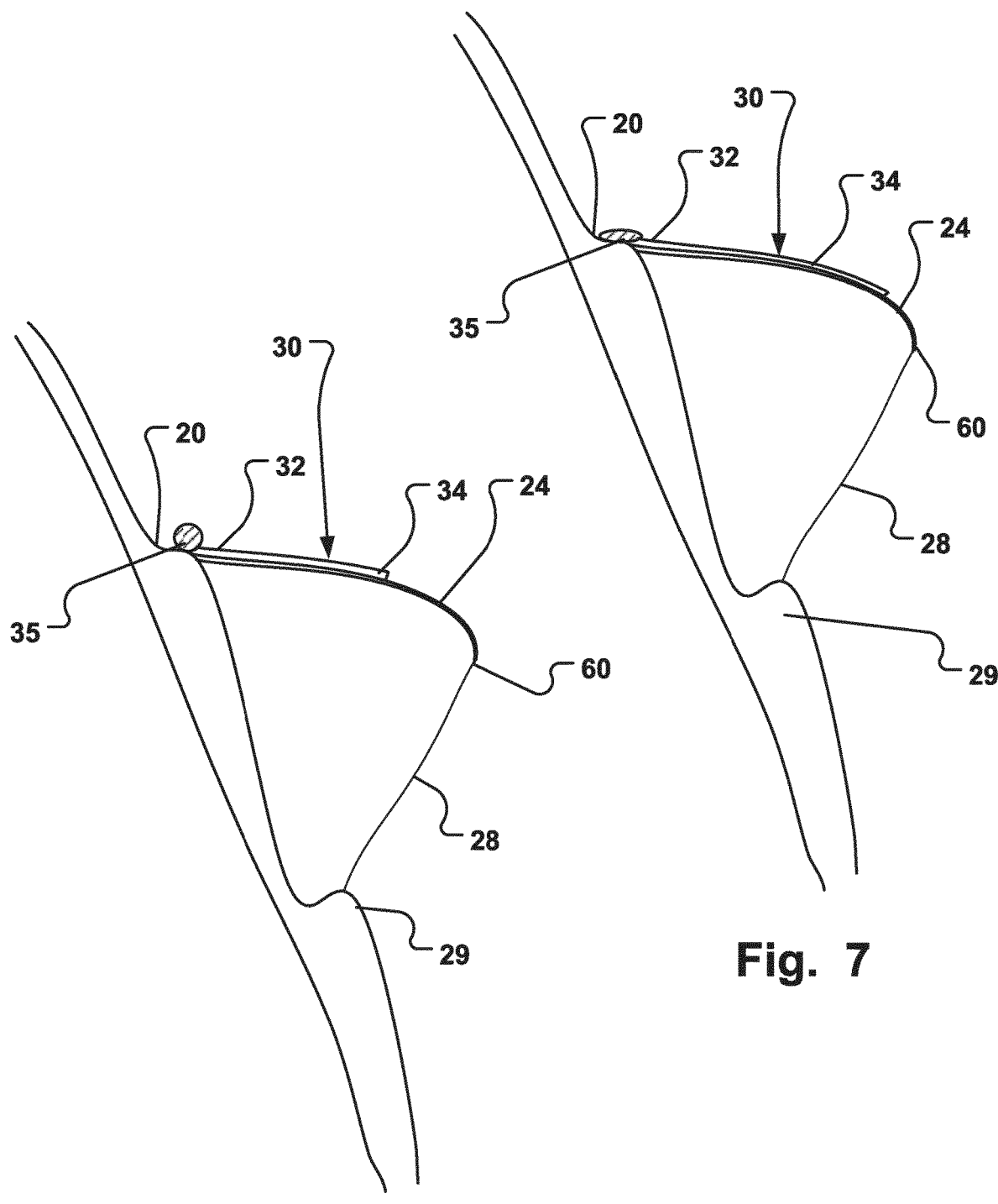
FIG. 6 is a cross-sectional view of half of a heart valve, illustrating the anatomic structures of heart wall, leaflet, chordae and papillary muscle.
FIG. 7 is another cross-sectional view of half of a heart valve, illustrating the anatomic structures of heart wall, leaflet, chordae and papillary muscle.

In an embodiment shown in FIG. 6, which is a cross-sectional view of half of a heart valve, the anatomic structures of the heart; the annulus 20, the leaflet 24, the chordae tendinae 28 and the papillary muscle 29 are shown. The flexible leaflet reinforcement patch 30 is in juxtaposition to the leaflet 24. The inner section 34 of the flexible leaflet reinforcement patch 30, the outer section 32 of the flexible leaflet reinforcement patch 30 and the anchoring unit 35 are also shown in FIG. 6. The inner section 34 of the flexible leaflet reinforcement patch 30 has an extension that optionally reaches and contacts the free edge 60 of the leaflet 24. Furthermore, in some embodiments there is a variation in thickness along the extension of the flexible leaflet reinforcement patch 30, towards the centre of the heart valve. Alternatively, the thickness of the flexible leaflet reinforcement patch 30 is circumferentially non-uniform, radially non-uniform or non-uniform in both circumferential and radial directions, i.e. the thickness of a first portion of the flexible leaflet reinforcement patch 30 can be non-uniform with a second portion of the flexible leaflet reinforcement patch 30, with the second portion of the flexible leaflet reinforcement patch 30 being positioned apart from the first portion of the flexible reinforcement patch 30 in any direction. FIGS. 6-9 illustrate variations of the extension and thickness of the flexible leaflet reinforcement patch 30 discussed in the description above. As can be seen in FIG. 6, the flexible leaflet reinforcement patch 30 can be short, and only extend from the anchoring unit 35 slightly further than halfway to the free edge 60 of the leaflet 24. In an embodiment according to FIG. 7, the flexible leaflet reinforcement patch 30 is long, and extends from the anchoring unit 35 considerably further than halfway to the free edge 60 of the leaflet 24, and almost to the free edge 60 of the leaflet 24. In some embodiments, such as the embodiment depicted in FIG. 9, the flexible leaflet reinforcement patch 30 extends from the anchoring unit 35 all the way to the free edge 60 of the leaflet 24.

In some embodiments, the anchoring unit 35 is a first loop-shaped support, which is configured to abut a first side of the heart valve, and a first leaflet reinforcement patch 30 is connected at a connection surface to the first loop-shaped support. The first leaflet reinforcement patch 30 has a leaflet in juxtaposition to a section of the leaflet reinforcement patch which is configured to be arranged in juxtaposition against at least a portion of at least one of the leaflets when the first loop-shaped support is abutting the heart valve. The connected leaflet reinforcement patch is configured to provide reinforcement to at least one of the leaflets.

Figures 8, 9:
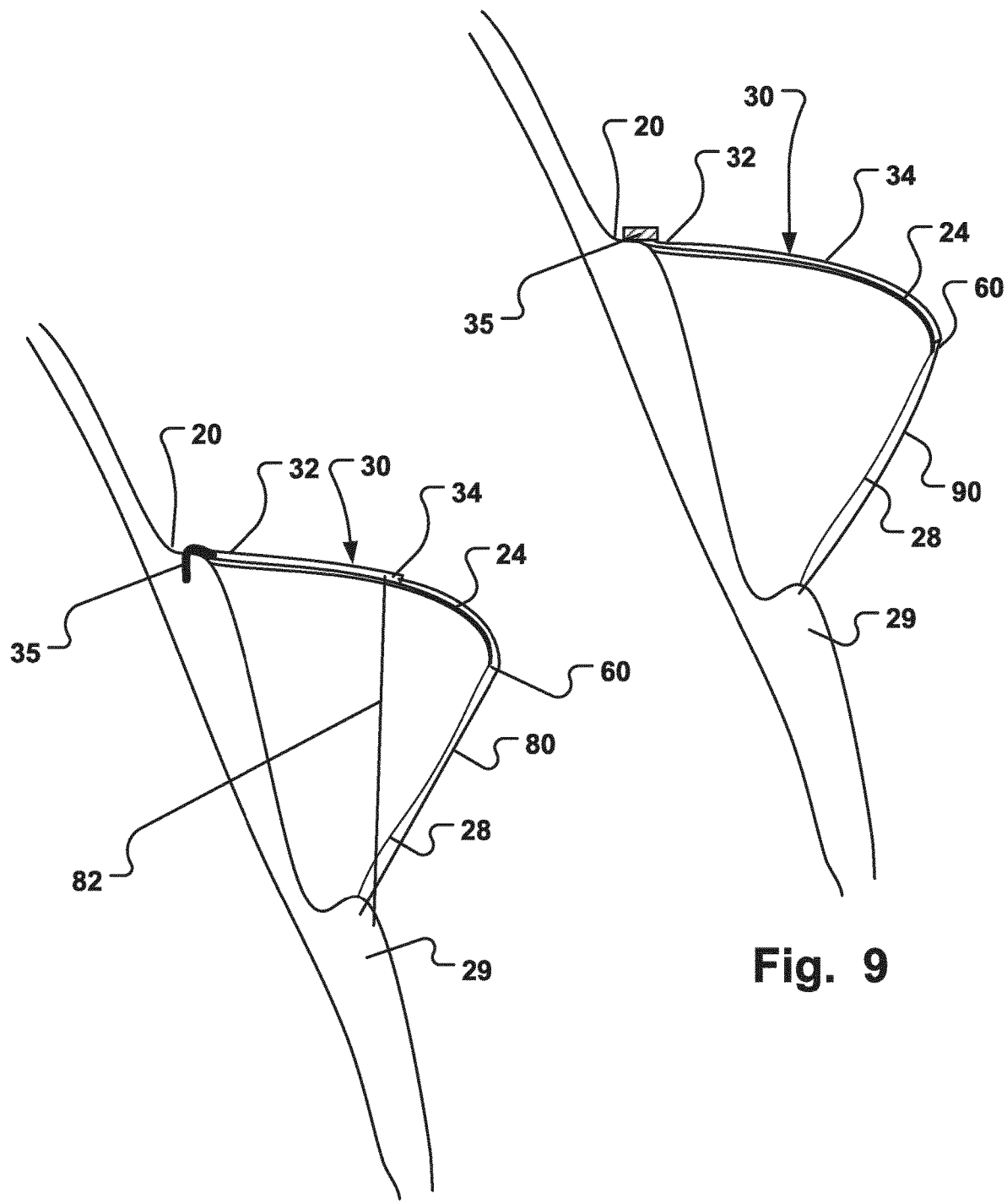
FIG. 8 is yet another cross-sectional view of half of a heart valve, illustrating the anatomic structures of heart wall, leaflet, chordae and papillary muscle.
FIG. 9 is a further cross-sectional view of half of a heart valve, illustrating the anatomic structures of heart wall, leaflet, chordae and papillary muscle.

It should be understood that the cross-section of the first loop-shaped support is not limited to a circular shape. FIGS. 6-9 illustrate variations of the anchoring unit 35. In FIG. 6, the anchoring unit 35 has an oval or conical shape. In FIG. 7, the anchoring unit 35 is substantially flat, with a square or rectangular cross-section and with rounded edges. FIG. 8 illustrates an anchoring unit with hooks positioned at the annulus 20. In FIG. 9, the anchoring unit 35 is substantially flat, with a square or rectangular cross-section. The anchoring unit 35 may also be of a different shape, such as spherical or conical. It should also be understood that the disclosure is not limited to the embodiments in the figures. As an example, the various shapes of the anchoring unit 35 given above can be used together with any of the flexible leaflet reinforcement patches, depicted in FIGS. 6-9, and being defined by their thickness and length.

In another embodiment according to FIG. 8 the flexible leaflet reinforcement patch 30 is configured for attaching a first end of at least one string 82 to the inner section 34. The inner section 34 is not required to fully extend to the free edge 60 of the leaflet 24 for connecting the first end of the string 82. In some embodiments the extension of the inner section 34 is proportional to the leaflet 24. The first end of the string 82 is either connected transversally through the leaflet 24 at the edge of the flexible leaflet reinforcement patch 30 or connected in such a manner that the string is positioned on the leaflet towards the free edge 60 of the leaflet 80. The other end of the string 82, the second end of at least one string 82, is in use to be connected to a cardiac structure other than a leaflet. The second end of the string 82 beneficially is connected to a cardiac structure within the left ventricle to preserve the natural movement of the leaflet as the heart beats. The structure may be the papillary muscle 29 or the lower parts of the corresponding chordae 28. This is advantageous, especially if the string 82 is secured with the free edge 60 of the leaflet 24, since then the natural leaflet can be preserved. The string 82 is important also when the chordae 28 has been damaged or degenerated, since the string can also function as a support for the chordae 28. In some embodiments the string 82 is made of a biocompatible material; however the string may also be of artificial and/or biological material. Some embodiments maintain the natural dynamics of the heart while replacing one or several chordae with one or several replacement units or strings 82 without substantial replacement of anatomic structures of the heart.

In another embodiment according to FIG. 9, the flexible leaflet reinforcement patch 30 has at least one string 90 extending from the inner section 34. The free end of the at least one string 90 is in use to be connected to a cardiac structure other than a leaflet 24, which may be a papillary muscle 29 or the lower parts of the corresponding chordae 28. This embodiment is beneficial, especially when the leaflet 24 is degenerated and/or damaged so that securing a string to the free edge 60 of the leaflet 24 is not possible. The embodiment also maintains the natural dynamics of the heart while adding one or several artificial chordae 28 or at least one string 90, as replacement or support, without substantial replacement of anatomic structures of the heart.

Figure 10:
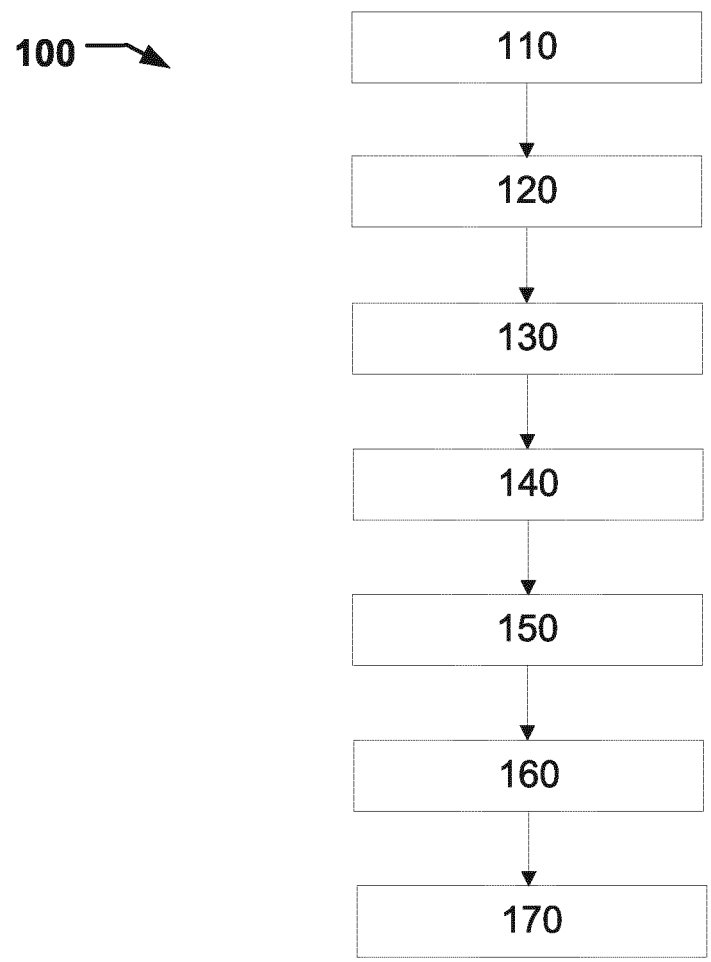
FIG. 10 is a flow chart of an embodiment of a method 100 comprising steps 110-170.

In FIG. 10, a method is illustrated for improving the function of a heart valve in sequential steps 100, although it should be apparent for a skilled person in the art when reading the present disclosure that same steps could be performed overlapping each other. It should also be understood that some steps may be performed simultaneously. The method begins with a leaflet-ectomy according to standard procedures or a sliding procedure 110. These procedures will alter the strength of the leaflet, since stitches, clamps and/or other connecting units are used to align the cut edges of the leaflets together with one another and/or with the annulus. The flexible leaflet reinforcement patch 30 is then placed and positioned 120 at the mitral valve with the outer section towards the annulus and the inner section 34 towards the centre of the valve. The flexible leaflet reinforcement patch 30 is rotated and adjusted to align 130 the portion in juxtaposition with the flexible leaflet reinforcement patch 30 to the desired position on the leaflet 24. If an anchoring unit 35 is connected to the flexible leaflet reinforcement patch 30, the anchoring unit 35 is secured 140 into the heart tissue in or adjacent to the annulus. If the portion in juxtaposition to the flexible leaflet reinforcement patch 30 has anchoring units 35, the anchoring units are secured 150 into the leaflet 24. Some procedures require replacement of one or several chordae 28 for the leaflet 24 to gain a more natural behaviour of the leaflet 24. Optionally, in step 160, one end of a string 80, 90 is attached to the inner section 34 of the flexible leaflet reinforcement patch 30, while the other end of the string 80, 90 is attached to a cardiac structure, such as a chordae 28 or a papillary muscle 29, within the left ventricle. Alternatively several strings, such as string 80 or string 90 can be attached. As another alternative, at least one string 80 is attached to a chordae 28 and at least one string 90 is attached to a papillary muscle 90. When the procedure is completed the heart is sealed or closed in step 170.

In the embodiments disclosed above, the anchoring unit 35 has only one loop-shaped support. However, it should be understood that the anchoring unit 35 in some embodiments also may have further loop-shaped supports.

Figure 11:
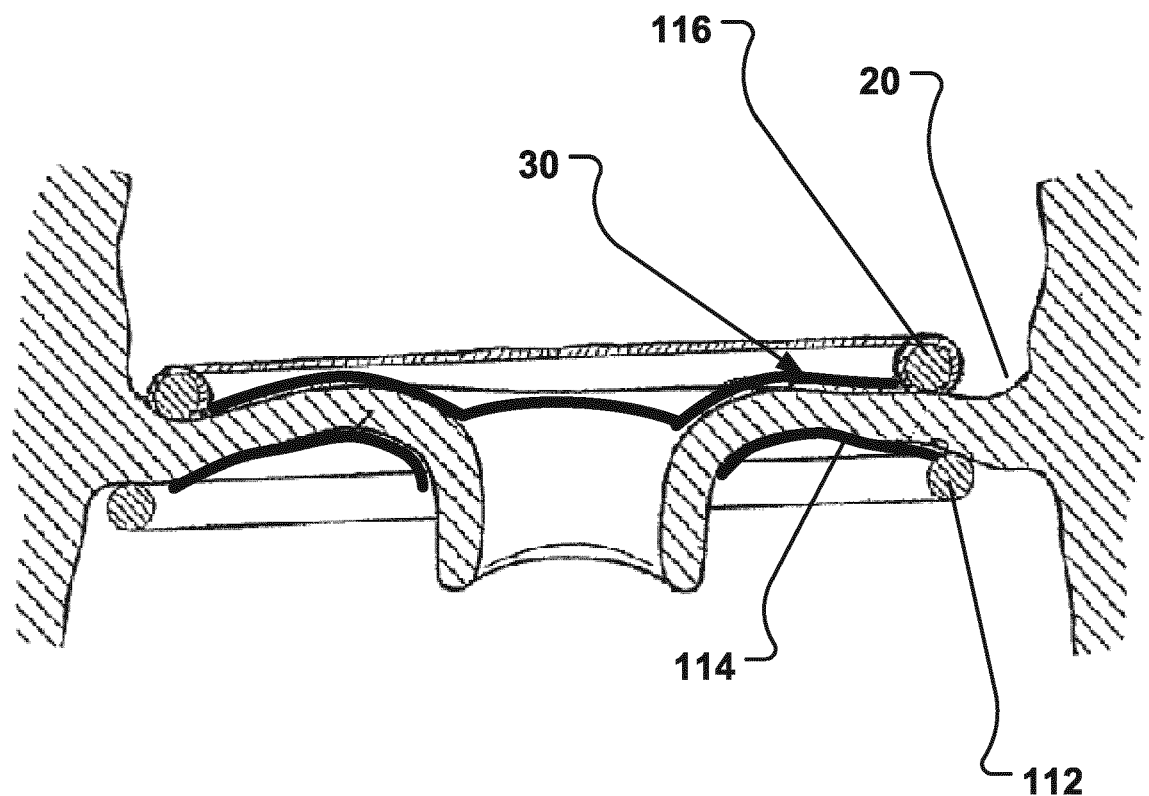
FIG. 11 is a cross-sectional view through a heart valve, illustrating placement of a flexible leaflet reinforcement patch.

FIG. 11 illustrates an embodiment; wherein a second flexible leaflet reinforcement patch 114 is put in juxtaposition with the leaflet 24 on the opposite side of the annulus 20 with respect to the first flexible leaflet reinforcement patch 30 and the first loop-shaped support 116. The second flexible leaflet reinforcement patch 114 is connected to a second tissue anchoring unit 112, such as a second loop-shaped support. The second loop-shaped support 112 and the second flexible leaflet reinforcement patch 114 are commonly positioned within the left ventricle. In other embodiments, any number of flexible leaflet reinforcement patches can be used.

The method above is not limited to open surgery; it should be clear for the skilled person in the art that a catheter-based procedure is within the scope of the method.

In one embodiment of this disclosure, a second flexible leaflet reinforcement patch 114 is positioned at a target site at an inside of a cardiac valve, preferably with an opposing first flexible leaflet reinforcement patch 30. The first flexible leaflet reinforcement patch 30 may be omitted in some embodiments. Due to the second flexible leaflet reinforcement patch 114, it will be possible to improve tightness of the valve and reduce or avoid leakage or regurgitation of the valve, since the second flexible leaflet reinforcement patch 114 will seal the valve area from the cardiac chamber towards the atrial side of the valve. The leaflet reinforcement is improved by the second flexible leaflet reinforcement patch 114, in particular during systolic high pressure in the cardiac chamber.

Regarding ways of entering the heart valve of interest both transapical, as well as through the arterial venous system are potential procedures for the method.

Another approach that can be taken is the epicardial access approach, which is an approach in which a device can be inserted via the left internal mammary puncture from the left arm, i.e. there is no need for any sub-xiphoid incision. Thus, the epicardial access approach is a minimally invasive approach.

The present disclosure has been described above with reference to specific embodiments. However, other embodiments than the above described are equally possible within the scope of the disclosure. Different method steps than those described above, may be provided within the scope of the disclosure. A radially outwardly oriented sealing flange may be added to an anchoring unit, in order to further improve sealing efficiency.

The different features and steps of the disclosure may be combined in other combinations than those described. The scope of the disclosure is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

What is claimed is:

1. A method for improving the function of a heart valve, the heart valve comprising valve tissue including an annulus at an outer segment of the valve tissue and a plurality of leaflets at an inner segment of the valve tissue, the method comprising:

placing a first flexible leaflet reinforcement patch to orient the an outer section thereof towards the annulus, the first flexible leaflet reinforcement patch having an extension between the outer section and an inner section and a varying thickness between the outer section and the inner section in an axial direction of the first flexible reinforcement patch, the outer section is connected to a tissue anchoring unit, the tissue anchoring unit comprises a first loop-shaped support, the first loop-shaped support comprises a loop that surrounds the inner section and the outer section, orienting the inner section of the first flexible leaflet reinforcement patch towards the plurality of leaflets, and placing at least one of said plurality of leaflets in juxtaposition with at least a portion of said inner section of the first flexible leaflet reinforcement patch so that the portion of said inner section provides reinforcement to at least one of said plurality of leaflets.

2. The method according to claim 1, wherein placing the first flexible leaflet reinforcement patch comprises attaching the tissue anchoring unit in said heart valve tissue such that the first flexible leaflet reinforcement patch extends from an inner periphery of the tissue anchoring unit towards a center of the heart valve.

3. The method according to claim 1, wherein said tissue anchoring unit provides an abutment against the whole extension of said annulus.

4. The method according to claim 1, wherein placing at least the portion of the inner section of the first flexible leaflet reinforcement patch in juxtaposition against the at least one of said plurality of leaflets comprises connecting at least one string to the first flexible leaflet reinforcement patch and a cardiac structure, other than a leaflet.

5. The method according to claim 1, comprising
connecting a first end of a string to said inner section of the first flexible leaflet reinforcement patch where the inner section is in juxtaposition with at least one of the plurality of leaflets,
connecting a second end of said string to chordae or a papillary muscle within a left ventricle.

6. The method according to claim 5, wherein the string is a chordae replacement unit.

7. The method according to claim 1, comprising arranging a second flexible leaflet reinforcement patch on an opposite side of said heart valve from said first leaflet reinforcement patch.

8. The method according to claim 7, comprising connecting the second flexible leaflet reinforcement patch to a second anchoring unit inside a left ventricle of the heart.

9. The method according to claim 1, comprising extending the first leaflet reinforcement patch from the tissue anchoring unit at least partly to a free edge of the at least one leaflet.

10. A method for improving the function of a heart valve, the heart valve comprising valve tissue including an annulus at an outer segment of the valve tissue and a plurality of leaflets at an inner segment of the valve tissue, the method comprising:

placing a first flexible leaflet reinforcement patch to orient an outer section thereof towards the annulus, the first flexible leaflet reinforcement patch having an extension between the outer section and an inner section and a varying thickness between the outer section and the inner section extending in a direction perpendicular to the annulus, the outer section is connected to a tissue anchoring unit, the tissue anchoring unit comprises a first loop-shaped support, the first loop-shaped support comprises a loop that surrounds the inner section and the outer section, orienting the inner section of the first flexible leaflet reinforcement patch towards the plurality of leaflets, and placing at least one of said plurality of leaflets in juxtaposition with at least a portion of said inner section of the first flexible leaflet reinforcement patch so that the portion of said inner section provides reinforcement to at least one of said plurality of leaflets.

* * * * *